US00PP30680P2

(12) United States Plant Patent
Wulfinghoff

(10) Patent No.: US PP30,680 P2
(45) Date of Patent: Jul. 9, 2019

(54) ***ALSTROEMERIA* PLANT NAMED 'ZOE'**

(50) Latin Name: *Alstroemeria hybrida*
Varietal Denomination: Zoe

(71) Applicant: Robert Paul Wulfinghoff, The Hague (NL)

(72) Inventor: Robert Paul Wulfinghoff, The Hague (NL)

(73) Assignee: Wulfinghoff Alstroemeria B.V., Rijswijk (NL)

( * ) Notice: Subject to any disclaimer, the term of this patent is extended or adjusted under 35 U.S.C. 154(b) by 0 days.

(21) Appl. No.: 15/932,849

(22) Filed: May 7, 2018

(51) Int. Cl.
*A01H 5/02* (2018.01)

(52) U.S. Cl.
USPC ..... Plt./309
CPC ..... *A01H 5/02* (2013.01)

(58) Field of Classification Search
USPC ..... Plt./309
CPC ..... A01H 5/0211
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Zoe', characterized by its compact and mounding plant habit; sturdy and strong plants; vigorous growth habit and moderate to rapid growth rate; freely branching habit; green and pale yellow green variegated leaves; light red-colored flowers with yellow-colored centers and dark-colored stripes; and good garden performance.

2 Drawing Sheets

Botanical designation: *Alstroemeria hybrida.*
Cultivar denomination: 'ZOE'.

BACKGROUND OF THE INVENTION

The present invention relates to a new and distinct cultivar of *Alstroemeria* plant, botanically known as *Alstroemeria hybrida*, typically grown as a container-type garden *Alstroemeria* and hereinafter referred to by the name 'Zoe'.

The new *Alstroemeria* plant is a naturally-occurring branch mutation of *Alstroemeria hybrida* 'Tara', disclosed in U.S. Plant Pat. No. 14,722. The new *Alstroemeria* plant was discovered and selected by the Inventor on a single plant within a population of plants of 'Tara' in a controlled greenhouse environment in Sussex, United Kingdom in 2014.

Asexual reproduction of the new *Alstroemeria* plant by in vitro rhizogenesis in a controlled greenhouse environment in Roelofarendsveen, The Netherlands since 2015 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Zoe'. These characteristics in combination distinguish 'Zoe' as a new and distinct *Alstroemeria* plant:

1. Compact and mounding plant habit.
2. Sturdy and strong plants.

3. Vigorous growth habit and moderate to rapid growth rate.
4. Freely branching habit.
5. Green and pale yellow green variegated leaves.
6. Light red-colored flowers with yellow-colored centers and dark-colored stripes.
7. Good garden performance.

Plants of the new *Alstroemeria* can be compared to plants of the mutation parent, 'Tara'. Plants of the new *Alstroemeria* differ primarily from plants of 'Tara' in leaf color as plants of 'Tara' have non-variegated leaves. In addition, plants of the new *Alstroemeria* have narrower leaves than plants of 'Tara'.

Plants of the new *Alstroemeria* can be compared to plants of the *Alstroemeria hybrida* 'Davina', disclosed in U.S. Plant Pat. No. 20,703. In side-by-side comparisons, The Netherlands, plants of the new *Alstroemeria* differ from plants of 'Davina' in the following characteristics:

1. Plants of the new *Alstroemeria* have smaller flowers than plants of 'Davina'.
2. Plants of the new *Alstroemeria* and 'Davina' differ in flower color as plants of 'Davina' have salmon pink and yellow-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Zoe' grown in container.

The photograph at the top of the second sheet is a close-up view of a typical flower of 'Zoe'.

The photograph at the bottom of the second sheet is a close-up view of typical leaves of 'Zoe'.

DETAILED BOTANICAL DESCRIPTION

The aforementioned photographs and following observations and measurements describe plants of the new *Alstroemeria* grown during the spring in four-liter containers in a glass-covered greenhouse in Maasdijk, The Netherlands and under cultural practices typical of commercial container-type *Alstroemeria* production. During the production of the plants, day temperatures averaged 18° C. and night temperatures averaged 8° C. Plants were 24 weeks old when the photographs were taken and 32 weeks old when the detailed description was taken. In the following description, color references are made to The Royal Horticultural Society Colour Chart, 2001 Edition, except where general terms of ordinary dictionary significance are used.

Botanical classification: *Alstroemeria hybrida* 'Zoe'.

Parentage: Naturally-occurring branch mutation of *Alstroemeria hybrida* 'Tara', disclosed in U.S. Plant Pat. No. 14,722.

Propagation:

*Type*.—By in vitro rhizogenesis.

*Root description*.—Medium in thickness, fleshy; close to 155B to 155C in color, actual color of the roots is dependent on substrate composition, water quality, fertilizers, substrate temperature and physiological age of roots.

*Rooting habit*.—Moderately freely branching; dense.

*Rhizome description*.—Shape: Elongate; rounded. Length: About 1 cm to 5 cm. Diameter: About 6 mm to 15 mm. Texture and luster: Smooth; matte. Color: Close to 158A to 158D.

Plant description:

*Plant and growth habit*.—Perennial garden plant; compact and mounded plant habit; freely branching habit, bushy appearance; sturdy and strong plants; vigorous growth habit; moderate to rapid growth rate.

*Plant height, soil to level to top of foliar plane*.—About 25 cm.

*Plant height, soil to level to top of floral plane*.—About 30 cm.

*Plant diameter* (*area of spread*).—About 27 cm to 35 cm.

Stem description:

*Aspect*.—Mostly upright.

*Internode length*.—About 0.5 cm to 3 cm.

*Strength*.—Moderately strong, sturdy.

*Texture and luster*.—Smooth, glabrous; matte.

*Color, when developing*.—Close to 144B to 144D.

*Color, fully developed*.—Close to 144B.

Leaf description:

*Arrangement*.—Alternate; below the peduncle, arranged in a single whorl; leaves sessile.

*Length*.—About 7 cm to 9 cm.

*Width*.—About 3 cm to 3.5 cm.

*Shape*.—Narrowly ovate to lanceolate.

*Apex*.—Acute to acuminate.

*Base*.—Rounded with attenuate tendencies.

*Margin*.—Entire; undulate.

*Texture and luster, upper surface*.—Smooth, glabrous; moderately glossy.

*Texture and luster, lower surface*.—Rough, glabrous; matte.

*Venation pattern*.—Parallel/pinnate.

*Color*.—Developing leaves, upper surface: Centers, close to 144B to 144C; surrounding the centers and towards the margins, close to 13 8A. Developing leaves, lower surface: Centers, close to 144B to 144C; surrounding the centers and towards the margins, close to 138B. Fully developed leaves, upper surface: Centers, close to 145C to 145D; surrounding the centers and towards the margins, close to 137A; venation, similar to lamina colors. Fully developed leaves, lower surface: Centers, close to 145C to 145D; surrounding the centers and towards the margins, close to 137B; venation, similar to lamina colors.

Flower description:

*Flower type and habit*.—Single cup-shaped flowers arranged in compound umbels; flowers face mostly outwardly; moderately freely flowering habit with about three to four flowers developing per inflorescence and about 20 to 100 flowers developing per plant.

*Natural flowering season*.—Flowering continuous from May to September in The Netherlands; early-flowering habit, plants begin flowering about 12 to 16 weeks after stem initiation.

*Fragrance*.—None detected.

*Flower longevity on the plant*.—About one to three weeks, longevity is temperature-dependent; flowers not persistent.

*Flower buds*.—Length: About 1.5 cm to 2.5 cm. Diameter: About 1 cm to 2 cm. Shape: Narrowly ovoid. Texture and luster: Smooth, glabrous; matte. Color: Close to 46A to 46B.

*Umbel height*.—About 7 cm.

*Umbel diameter*.—About 7 cm.

*Flower diameter*.—About 4 cm to 6 cm.

*Flower depth* (*height*).—About 3.5 cm to 4 cm.

*Perianth*.—Arrangement: Six arranged in two whorls, each whorl with two lateral and one median segments. Size, inner perianth: Length, lateral segments: About 4.5 cm. Width, lateral segments: About 1.4 cm. Length, median segment: About 4.2 cm. Width, median segment: About 1.3 cm. Size, outer perianth: Length, lateral segments: About 4 cm to 6 cm. Width, lateral segments: About 3 cm to 4 cm. Length, median segment: About 4 cm to 6 cm. Width, median segment: About 3 cm to 4 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Emarginate, wishbone-shaped. Base, inner perianth, lateral and median segments: Attenuate. Base, outer perianth, lateral and median segments: Cuneate. Margin, inner perianth, lateral and median segments: Entire. Proximally, entire; distally, finely serrate. Margin, outer perianth, lateral and median segments: Proximally, entire; distally, finely serrate. Texture and luster, inner and outer perianths, lateral and median segments: Smooth, glabrous; matte, dull. Color, inner perianth, lateral segments: When opening, upper surface: Distally, close to 47B to 47C; proximally, close to 13A to 13D; stripes, close to 202A. When opening, lower surface: Distally, close to 50B to 50C; proximally, close to 12A to 12D. Fully opened, upper surface: Distally, close to 47A to 47B; proximally, close to 13A to 13B; stripes, close to 202A; colors becoming closer to 47A and 13A with development. Fully opened, lower surface: Distally, close to 50A to 50B; proximally, close to 12A to 12B; colors becoming closer to 50A and 12A with development. Color, inner perianth, median segment: When opening, upper surface: Distally, close to 47B to 47C; proximally, close to 13A to 13D; stripes, close to 202A. When opening, lower surface: Distally, close to 50B to 50C; proximally, close to 12A to 12D. Fully opened, upper surface: Distally, close to 47A to 47B; proximally, close to 13A to 13B; stripes, close to 202A; colors becoming closer to 47A and 13A with development. Fully opened, lower surface: Distally, close to 50A to 50B; proximally, close to 12A to 12B; color becoming closer to 50A and 12A with development. Color, outer perianth, lateral and median segments: When opening, upper surface: Close to 47B to 47C. When opening, lower surface: Close to 50B to 50C. Fully opened, upper surface: Close to 47A to 47B; color becoming closer to 47A with development. Fully opened, lower surface: Close to 50A to 50B; color becoming closer to 50A with development.

*Pedicels*.—Length: About 1.4 cm to 2.4 cm. Diameter: About 2.5 mm. Strength: Strong. Angle: Erect to about 40° from vertical. Texture and luster: Smooth, glabrous; matte. Color, upper and lower surfaces: Close to 144C to 144D.

*Reproductive organs*.—Stamens: Quantity per flower: Six. Filament length: About 4 cm. Filament color: Close to 50A to 50B. Anther size: About 1.5 cm by 5 cm. Anther shape: Oval. Anther color: Close to 13A. Pollen amount: Abundant. Pollen color: Close to 162A. Pistils: Quantity per flower: One. Pistil length: About 3 cm. Style length: About 2.5 cm. Style color: Close to 56A to 56C. Stigma shape: Tri-parted. Stigma diameter: About 1.5 cm. Stigma color: Close to 56A to 56C. Ovary color: Close to 56A to 56C.

*Fruits*.—Length: About 1 cm. Diameter: About 7 mm. Texture: Smooth. Color: Close to 144A.

*Seeds*.—To date, seed development has not been observed on plants of the new *Alstroemeria*.

Disease & pest resistance: To date, plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 1° C. to about 30° C.

It is claimed:

1. A new and distinct *Alstroemeria* plant named 'Zoe' as illustrated and described.

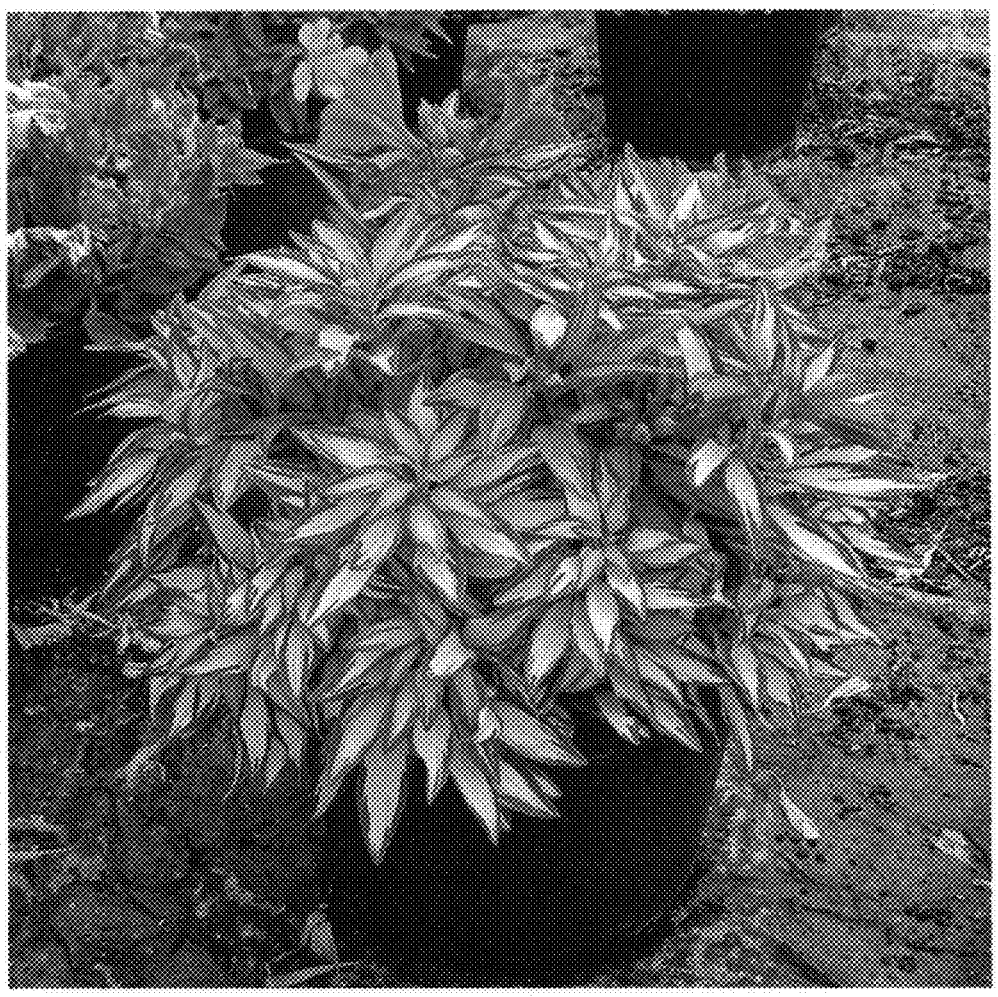

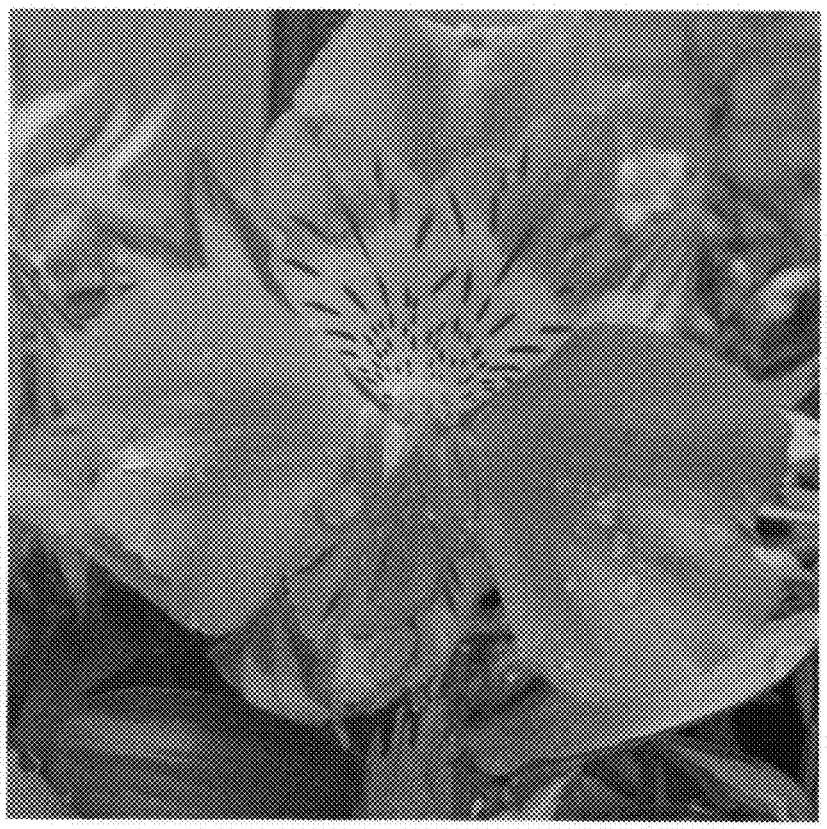
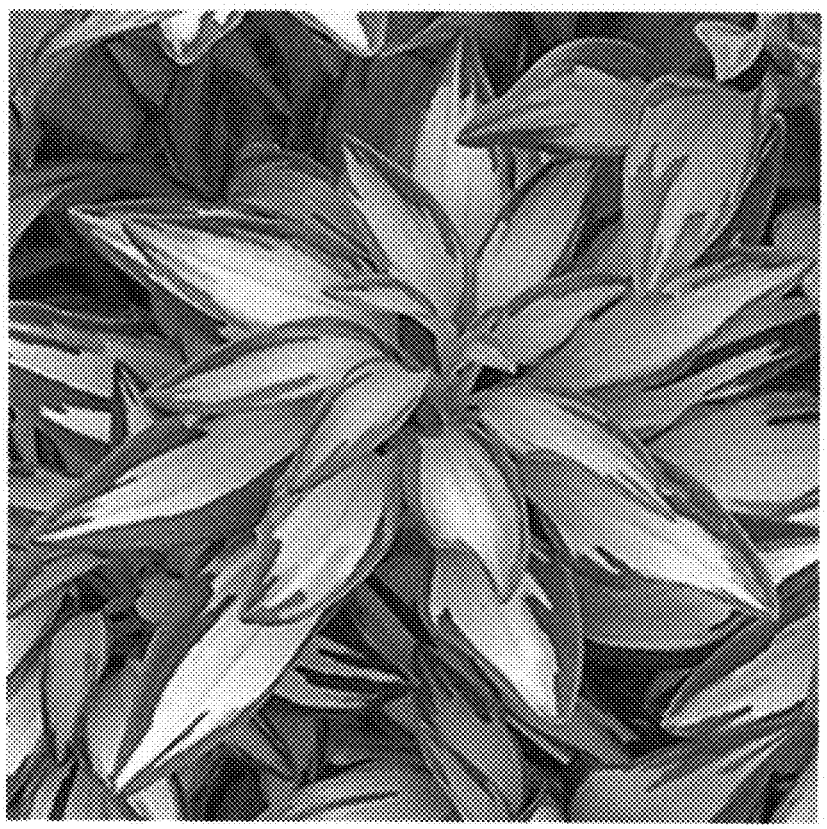

* * * * *